US010935441B2

(12) United States Patent
Kumar et al.

(10) Patent No.: US 10,935,441 B2
(45) Date of Patent: Mar. 2, 2021

(54) WEARABLE DEVICE TO INDICATE HAZARDOUS CONDITIONS AND A METHOD THEREOF

(71) Applicant: WIPRO LIMITED, Bangalore (IN)

(72) Inventors: Vijay Kumar, Bangalore (IN); Thomas Chittakattu Ninan, Angadikadavu (IN); Shagun Rai, Allahabad (IN)

(73) Assignee: Wipro Limited, Bangalore (IN)

( * ) Notice: Subject to any disclaimer, the term of this patent is extended or adjusted under 35 U.S.C. 154(b) by 664 days.

(21) Appl. No.: 15/817,433

(22) Filed: Nov. 20, 2017

(65) Prior Publication Data
US 2019/0086275 A1 Mar. 21, 2019

(30) Foreign Application Priority Data

Sep. 21, 2017 (IN) .............................. 201741033527

(51) Int. Cl.
*G01K 11/12* (2006.01)
*A61B 5/00* (2006.01)
*G01K 1/02* (2021.01)
*A61B 5/11* (2006.01)
*G01K 13/00* (2021.01)
*G01K 1/04* (2006.01)
*A42B 3/04* (2006.01)

(52) U.S. Cl.
CPC ............ *G01K 11/12* (2013.01); *A61B 5/1112* (2013.01); *A61B 5/6803* (2013.01); *G01K 1/02* (2013.01); *G01K 1/045* (2013.01); *G01K 13/002* (2013.01); *A42B 3/046* (2013.01)

(58) Field of Classification Search
CPC ................ G01K 11/12; G01K 1/045
See application file for complete search history.

(56) References Cited

U.S. PATENT DOCUMENTS

| 7,528,737 | B2 * | 5/2009 | Hedtke ................ G01K 11/165 340/870.01 |
| 2010/0012017 | A1 * | 1/2010 | Miller ..................... G01J 1/429 116/201 |
| 2014/0208487 | A1 | 7/2014 | Orientale et al. |
| 2016/0291638 | A1 * | 10/2016 | Fu .......................... A61B 5/021 |

FOREIGN PATENT DOCUMENTS

| CN | 203012909 | | 6/2013 | |
| GB | 2384556 | * | 7/2003 | ............. G01K 11/12 |

* cited by examiner

*Primary Examiner* — Daniel S Larkin
(74) *Attorney, Agent, or Firm* — Finnegan, Henderson, Farabow, Garrett & Dunner, LLP

(57) ABSTRACT

The present disclosure discloses a wearable device to indicate a hazardous condition. The said device comprises one or more thermochromic paint coating layers, each indicative of a colour based on variations in temperature, one or more thermoelectric couples to regulate the temperature of corresponding one or more thermochromic paint coating layers, and a control module. The control module is configured to receive one or more parameters from one or more sensors associated with the one or more thermoelectric couples, determine one of presence and absence of at least one hazardous condition by comparing the one or more parameters with corresponding threshold parameters and configure the one or more thermoelectric couples to regulate temperature of the corresponding one or more thermochromic paint coating layers and to dynamically control indication of the colour, based on one of the presence and absence of the at least one hazardous condition.

16 Claims, 4 Drawing Sheets

WEARABLE DEVICE TO INDICATE HAZARDOUS CONDITIONS AND A METHOD THEREOF

TECHNICAL FIELD

The present disclosure relates to a wearable device. More particularly, but not specifically, the present disclosure relates to a wearable device used to indicate hazardous conditions.

BACKGROUND

Safety of a worker is an important factor that is implemented in industries. In the current scenario, it is very essential to monitor every worker working in a workplace to regulate workplace safety issues. The employers should take reasonable care of the safety of their workers. With the advent of technology, industries have implemented new and efficient safety solutions. These solutions are integrated to a device which may be present with the workers. For instance, the device can be a helmet, a glove or a hat. The solutions involve indicating the presence of the workers in the workplace, tracking mechanisms to track the worker in a workplace, intimating a monitoring station, about the presence of the workers in the workplace.

Few existing systems, use a hat with tracking mechanism, which may include a Radio-Frequency Identification (RFID) tag. The tracking mechanism is used to validate and monitor the presence of workers on a job site.

Few other systems use a helmet with a wireless camera and infrared indicators. The few other systems, also use a wireless video server, a monitoring station and a short message gateway with alarming function all integrated with Wireless Fidelity (Wi-Fi) technology. Image analysis software is employed to identify each worker wearing the helmet and hence helps to monitor the presence of workers on a job site.

The existing systems work with technologies such as Wi-Fi, RFID and other wireless technologies. The workers may be apprehensive about wearing these devices involving Radio Frequency (RF) technologies like Wi-Fi, Bluetooth as it may cause harm to the person using it.

The information disclosed in this background of the disclosure section is only for enhancement of understanding of the general background of the invention and should not be taken as an acknowledgement or any form of suggestion that this information forms the prior art already known to a person skilled in the art.

SUMMARY

In an embodiment, the present disclosure discloses a wearable device to indicate hazardous condition. The wearable device comprises one or more thermochromic paint coating layers, each indicative of a colour based on variations in temperature, one or more thermoelectric couples to regulate the temperature of corresponding one or more thermochromic paint coating layers and a control module. The control module is configured to receive one or more parameters from one or more sensors associated with the wearable device, determine one of presence and absence of at least one hazardous condition by comparing the one or more parameters with corresponding threshold parameters and configure the one or more thermoelectric couples to regulate temperature of the corresponding one or more thermochromic paint coating layers and dynamically control indication of the colour, based on one of the presence and absence of the at least one hazardous condition.

In an embodiment, the present disclosure discloses a method of indicating hazardous conditions on a wearable device. The method comprises receiving, by a control module of the wearable device, one or more parameters, from one or more sensors associated with the wearable device; determining, one of presence and absence of at least one hazardous condition by comparing the one or more parameters with corresponding threshold parameters and configuring, one or more thermoelectric couples to regulate temperature of corresponding one or more thermochromic paint coating layers, to dynamically control indication of colour, based on one of the presence and absence of the at least one hazardous condition.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING DRAWINGS

The novel features and characteristic of the disclosure are set forth in the appended claims. The disclosure itself, however, as well as a preferred mode of use, further objectives and advantages thereof, will best be understood by reference to the following detailed description of an illustrative embodiment when read in conjunction with the accompanying figures. One or more embodiments are now described, by way of example only, with reference to the accompanying figures wherein like reference numerals represent like elements and in which:

Figure 1:
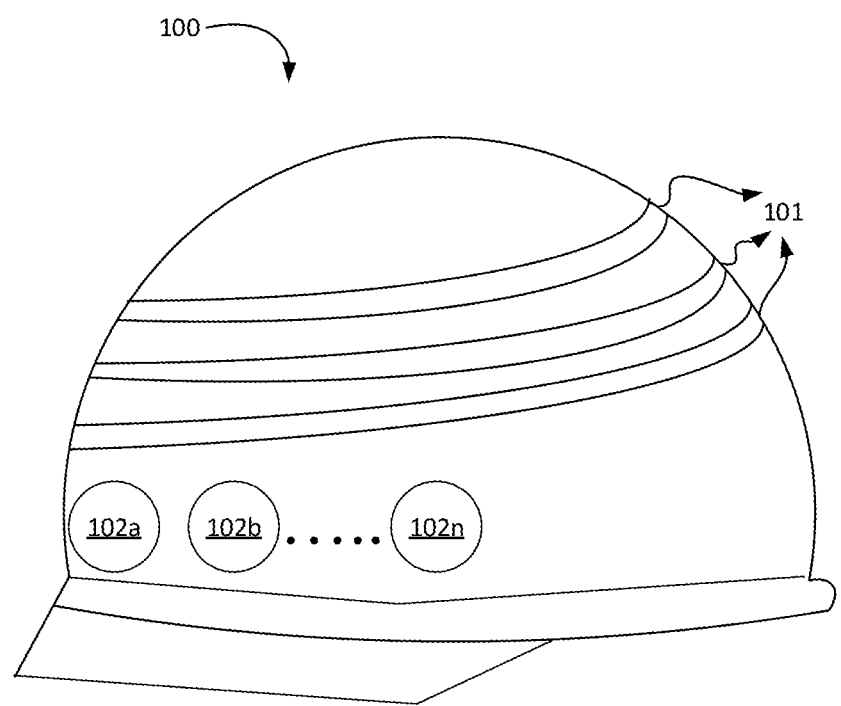
FIG. 1 shows a wearable device for indicating hazardous conditions in accordance with some embodiments of the present disclosure.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or apparatus.

Embodiments of the present disclosure relate to a wearable device for indicating hazardous conditions. The wearable device comprises one or more thermochromic paint coating layers, each indicative of a colour based on variations in temperature, one or more thermoelectric couples to regulate the temperature of corresponding one or more thermochromic paint coating layers and a control module. The control module controls the indication of a colour based on presence or absence of at least one hazardous condition, determined using one or more sensors associated with the wearable device.

FIG. 1 shows a wearable device 100. The wearable device 100 comprises an indication unit 101 and a sensor 102a, a sensor 102b, . . . , a sensor 102n. The sensor 102a, the sensor 102b, . . . , and the sensor 102n, can be represented as one or more sensors 102 hereafter in the present disclosure. The wearable device 100 may be capable of determining one of presence and absence of at least one hazardous condition by detecting one or more parameters and comparing the one or more parameters with corresponding threshold parameters. The wearable device 100 further provides an indication if at least one hazardous condition is determined based on the comparison. The indication may be a colour. The one or more sensors 102 may be used for detecting the one or more parameters. The detected parameter is provided as input to the indication unit 101. The indication unit 101 receives the one or more parameters and determines one of presence and absence of at least one hazardous condition. The indication unit 101 may provide a colour indication when at least one hazard is detected.

In an embodiment, the wearable device 100 may be one of a watch, a helmet, spectacles, a hard hat, a wrist band, a head band, any clothing or any other device or cosmetic which could be worn by a user. A person skilled in the art would understand that the wearable device 100 may be any other device, not mentioned explicitly in the present disclosure.

In an embodiment, the one or more parameters, may include, but are not limited to environmental parameters and user parameters. The environmental parameters may include, but are not limited to, ambience temperature level, hazardous gas level and user location. The user parameters may include, but are not limited to, user respiration rate, blood oxygen levels, heart rate, body temperature and user topple.

In an embodiment, the one or more sensors 102 comprises at least one of, but are not limited to, a temperature sensor, a gas sensor, an accelerometer, a vibration sensor, a magnetometer, a core body temperature sensor, a heart rate sensor, a respiration rate sensor, a Saturation of Peripheral Oxygen ($SPO_2$) sensor. The wearable device 100 may be compatible with any type of sensors.

In an embodiment, the temperature sensor, the gas sensor, the magnetometer may be used to determine the environmental parameters. The temperature sensor may be used for detecting the ambient temperature level. The gas sensor may be used to detect the leakage of hazardous gases. The magnetometer may be used to measure magnetic field around the user, used in detecting the location of the user.

In an embodiment, the core body temperature sensor, the heart rate sensor, the respiration rate sensor, the $SPO_2$ sensor may be used to determine the user parameters. The core body temperature sensor may be used to determine the body temperature of the user. The heart rate sensor may be used to determine the heart rate of the user. The respiration rate sensor may be used to determine rate of respiration of the user. The $SPO_2$ sensor may be used to determine the blood oxygen levels of the user. The accelerometer may be used to determine any kind of motion, for instance user topple.

In an embodiment, the at least one hazard may be due to variation of one of the environmental parameters and user parameters, from a predefined threshold level. The indication unit 101 compares the one or more parameters with the corresponding threshold level. If the detected one or more parameters varies from the corresponding threshold level, the indication unit 101 determines at least one hazardous condition based on the variation and provides the indication. The indication may be a colour based on the detected at least one hazard. For instance, a user topple may be determined as the at least one hazardous condition and may be indicated by representation of blue colour on the wearable device 100. The wearable device 100 may he integrated with any other units which provide an indication.

Figure 2:
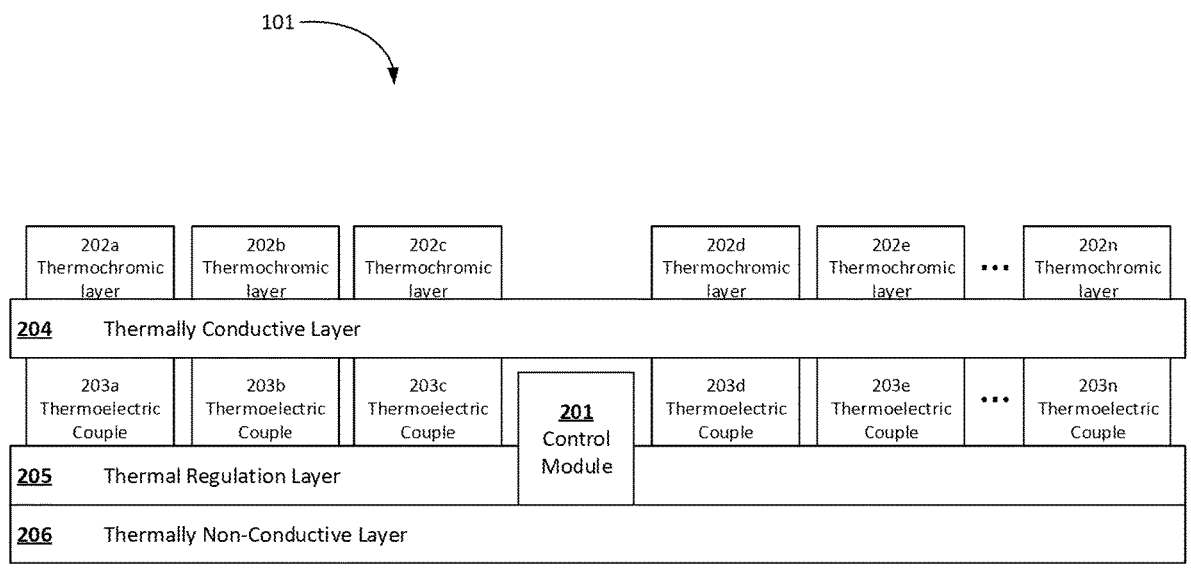
FIG. 2 shows an exemplary block diagram of an indication unit associated with a wearable device for indicating hazardous condition in accordance with some embodiments of the present disclosure.

FIG. 2 illustrates block diagram of the indication unit 101 associated with the wearable device 100. The indication unit 101 comprises of a control module 201, a thermochromic paint coating layer 202a, a thermochromic paint coating layer 202b, a thermochromic paint coating layer 202c, a thermochromic paint coating layer 202d, a thermochromic paint coating layer 202e . . . , a thermochromic paint coating layer 202n, a thermoelectric couple 203a, a thermoelectric couple 203b, a thermoelectric couple 203c, a thermoelectric couple 203d, a thermoelectric couple 203e, . . . , a thermoelectric couple 203n, a thermally conductive layer 204, a thermal regulation layer 205 and a thermally non-conductive layer 206. The thermochromic paint coating layer 202a, the thermochromic paint coating layer 202b, the thermochromic paint coating layer 202c, the thermochromic paint coating layer 202d, the thermochromic paint coating layer 202e . . . , and the thermochromic paint coating layer 202n can be represented as one or more thermochromic paint coating layers 202 hereafter in the present disclosure. The thermoelectric couple 203a, the thermoelectric couple 203b, the thermoelectric couple 203c, the thermoelectric couple 203d, the thermoelectric couple 203e . . . , and the thermoelectric couple 203n can be represented as one or more thermoelectric couples 203 hereafter in the present disclosure.

In an embodiment, the one or more thermochromic paint coating layers 202 may be present on an outer surface of the wearable device 100. The one or more thermochromic paint coating layers 202 works on the property of thermochromism. Thermochromism is a property of substances to indicate colour at a particular temperature. In an embodiment, the one or more thermochromic paint coating layers 202 absorbs heat and indicates a colour, in absence of heat, the thermochromic paint coating layer 202 remains transparent. Each of the one or more thermochromic paint coating layers 202 may be designed to emit a particular colour at a particular temperature. Each colour may indicate a particular hazard. Each of the one or more thermochromic paint coating layers 202 receives heat from the corresponding one or more thermoelectric couples 203 as shown in FIG. 2. For an instance, a hazardous gas leakage may be associated with red colour. Whenever a gas leakage is detected, the indication unit 101 configures the one or more thermoelectric couples 203 to regulate the temperature of the corresponding one or more thermochromic paint coating layer 202 for emitting the red colour.

In an embodiment, each of the one or more thermoelectric couples 203 may be present below the one or more thermochromic paint coating layer 202. The one or more thermoelectric couples 203 works on the principle of thermoelectric effect. The thermoelectric effect creates a temperature difference by transferring heat between two electrical junctions (not shown in the figure). A voltage is applied across two electrical junctions to create an electric current. When the current flows through the two electrical junctions, heat is dissipated at one junction and the other junction is relatively cooler. For example, the two junctions may be named a first junction and a second junction. In an instance, when the first junction is provided with a positive voltage and the second junction is provided with a negative voltage, temperature of the first junction increases compared to the second junction. In the above-mentioned instance, when the polarity is reversed the first junction dissipates heat towards the second junction thereby getting cooler compared to the second junction.

In an embodiment, the first junction may be associated with the corresponding one or more thermochromic paint coating layers 202 and the second junction may be associated with the thermal regulation layer 205. The one or more thermoelectric couples 203 increases the temperature of the corresponding one or more thermochromic paint coating layers 202 depending on the determined hazard to indicate a colour. The one or more thermoelectric couples 203 decreases the temperature of the corresponding one or more thermochromic paint coating layers 202 to remove the indication of the colour when the determined hazard is resolved.

In an embodiment, the thermally conductive layer 204 may be present between the one or more thermoelectric couples 203 and the corresponding one or more thermochromic paint coating layers 202 for propagating heat from the one or more thermoelectric couples 203 to the corresponding one or more thermochromic paint coating layers 202.

In an embodiment, the thermal regulation layer 205 may be present below the second junction of the one or more thermoelectric couples 203. The thermal regulation layer 205 may be used as a heat dissipating layer. The thermal regulation layer 205 may be used to absorb the heat from the second junction of the one or more thermoelectric couples 203.

In an embodiment, the control module 201 determines the presence or absence of hazard by comparing the one or more parameters received from the one or more sensors 102, with the corresponding threshold level. The control module 201 further configures the one or more thermoelectric couples 203 to regulate temperature of the corresponding one or more thermochromic paint coating layers 202, to dynamically control indication of the colour, based on one of the presence and absence of the at least one hazardous condition.

In an embodiment, on determining the presence of the at least one hazardous condition, the control module 201 provides a voltage to the corresponding one or more thermoelectric couples 203 such that the first junction of the corresponding one or more thermoelectric couples 203 associated with the one or more thermochromic paint coating layers 202 dissipates heat. The dissipation of the heat increases the temperature of the corresponding one or more thermochromic paint coating layers 202, to indicate the particular colour. When the determined at least one hazardous condition has been resolved, the control module 201 provides a reverse voltage to the corresponding one or more thermoelectric couples 203 such that the first junction of the corresponding one or more thermoelectric couples 203 associated with the one or more thermochromic paint coating layers 202 cools down. The cooled first junction of the corresponding one or more thermoelectric couples 203 instantly decreases the temperature of the corresponding one or more thermochromic paint coating layers 202, to remove the colour displayed. Thus, implying that the determined at least one hazardous condition has been resolved. For instance, in a workplace, if a worker topples wearing the wearable device 100, the accelerometer provides acceleration data to the control module 201. The control module 201 detects a fail and provides as indication of particular colour on the wearable device 100. When the control module 201 detects that the person has recovered and continues his work, the indication can be removed immediately.

In an embodiment, the indication of the colour, depends on the polarity of voltage provided by the control module 201 to the corresponding one or more thermoelectric couples 203. Presence or absence of the at least one hazardous condition can be instantly indicated by changing the polarity of the voltage provided by the control module 201 to the corresponding one or more thermoelectric couples 203. This provides flexibility to either increase or decrease the temperature of the corresponding one or more thermochromic paint coating layers 202, to indicate or remove the particular colour depending on one of the presence and absence of the at least one hazardous condition.

In an embodiment, the thermally non-conducive layer 206 may be present below thermal regulation layer 205. The thermally non-conductive layer 206 may prevent temperature changes from affecting the user of the wearable device.

Figure 3:
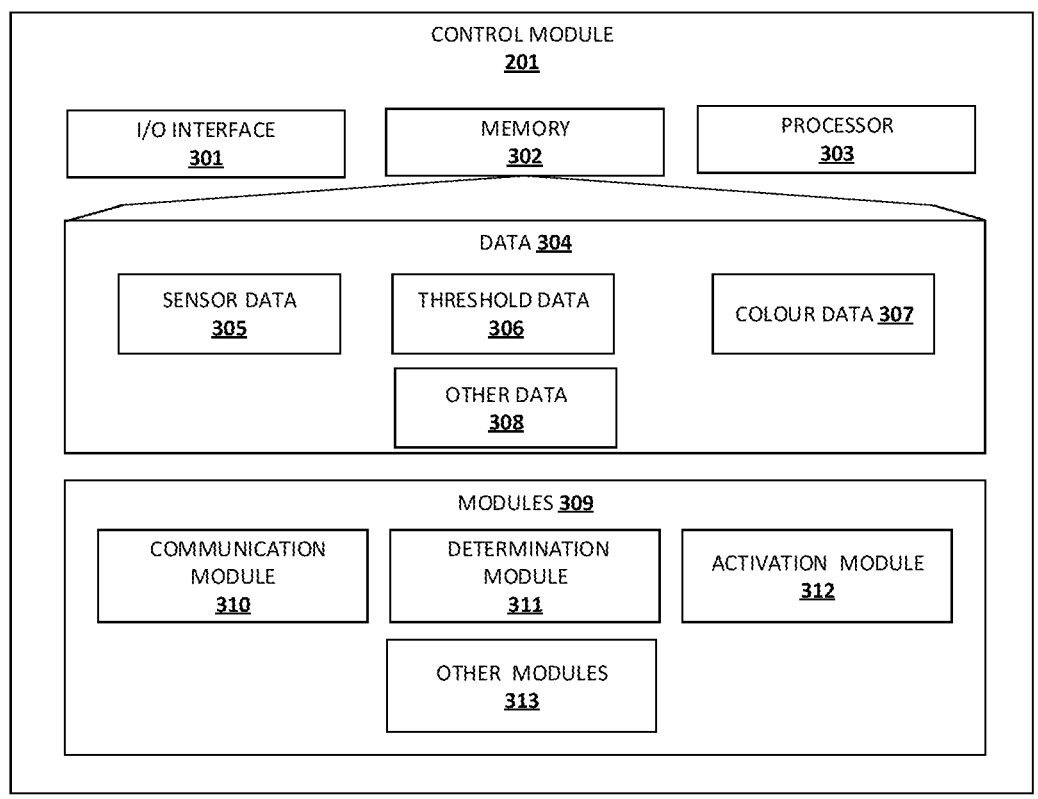
FIG. 3 shows internal architecture of a control module associated with a wearable device for indicating hazardous conditions in accordance with some embodiments of the present disclosure.

FIG. 3 illustrates the control module 201 associated with the wearable device in accordance with some embodiments of the present disclosure. The control module 201 may include at least one processor 303 and a memory 302 storing instructions executable by the at least one processor 303. The processor 303 may comprise at least one data processor for executing program components for executing user or system-generated requests. The memory 302 may be communicatively coupled to the processor 303. The control module 201 further comprises an Input/Output (I/O) interface 301.

In an embodiment, the I/O interface 301 may be coupled with the processor 303 through which an input signal or/and an output signal is communicated. The I/O interface 301 facilitates the connection of the one or more thermoelectric couples 203 with the control module via electric connections.

In an embodiment, data 304 may be stored within the memory 302. The data 304 may include, for example, sensor data 305, threshold data 306, colour data 307 and other data 308.

In an embodiment, the sensor data 305 may include the one or more parameters sensed by the one or more sensors 102. The values obtained from each of the one or more sensors 102 are stored in the sensor data 305.

In an embodiment, the threshold data 306 may include threshold values associated with each of the one or more hazardous conditions. These values are used to determine one of presence and absence of the at least one hazardous condition. The one or more parameters sensed by the sensors are retrieved by the processor 303 from the sensor data 305. The one or more parameters are compared with the corresponding threshold values.

In an embodiment, each of the hazardous conditions may be indicated by a particular colour. The colour data 307 may include data related to assignment of each of the hazardous conditions with a particular colour and may also include the identity (ID) of the corresponding one or more thermoelectric couples 203 to be configured.

In an embodiment, the other data 308 may include the location ID of one or more hazardous locations present in a workplace. The other data 308 may also include the data pertaining to the current location of the user obtained from a localization module. The other data 308 may include any other data additional to the above-mentioned data.

In an embodiment, the data 304 in the memory 302 is processed by modules 309 of the control module 201. As used herein, the term module refers to an application specific integrated circuit (ASIC), an electronic circuit, a field-programmable gate arrays (FPGA), Programmable System-on-Chip (PSoC), a combinational logic circuit, and/or other suitable components that provide the described functionality. The modules 309 when configured with the functionality defined in the present disclosure will result in a novel hardware.

In one implementation, the modules 309 may include, for example, a communication module 310, a determination module 311, an activation module 312 and other modules 313. It will be appreciated that such aforementioned modules 309 may be represented as a single module or a combination of different modules.

In an embodiment, the communication module 310 receives one or more parameters from the one or sensors 102 associated with the wearable device 100. The received one or more parameters are stored as the sensor data 305.

In an embodiment, the determination module 311 determines one of presence and absence of at least one hazardous condition. The one of presence and absence of at least one hazardous condition is determined by comparing the one or more parameters with the corresponding one or more threshold values. The comparison may show if the one or more parameters have varied from the corresponding one or more threshold values. The variation is used to determine one of presence and absence of at least one hazardous condition. For instance, the threshold value for temperature variation is 50° C. The temperature sensor measures a temperature of 52° C. The determination module 311 compares the measured value of 52° C. with the threshold value of 50° C. As the measured value is more than the threshold value, the determination module 311 determines this condition as hazardous.

In an embodiment, the activation module 312 configures the one or more thermoelectric couples 203 to regulate temperature of the corresponding one or more thermochromic paint coating layers 202, to dynamically control indication of the colour, based on one of the presence and absence of the at least one hazardous condition. Each of the one or more thermoelectric couples 203 are connected to the I/O interface 301. The activation module 312 activates the corresponding one or more thermoelectric couples 203 by providing appropriate voltage through the I/O interface 301 to indicate a particular colour. Each of the one or more thermoelectric couples 203 is associated with the corresponding one or more thermochromic paint coating layers 202 indicating a particular colour. When the at least one hazard is determined, the activation module 312 configures at least one thermoelectric couples from the one or more thermoelectric couples 203 to activate the corresponding one or more thermochromic paint coating layers 202 designed to emit the colour assigned to the particular hazard. This data is obtained from the colour data 307.

In an embodiment, the other modules 313 may include, but are not limited to, a localization module and an alert module. The localization module provides the location information of the user. The location information may be based on geo-magnetic location, or any other non-radiating techniques. The magnetometer may be used to determine the location of the user. Based on the location of the user the wearable device indicates a particular colour. For an instance, when the user is 20 m away from a predetermined hazardous location, the determination module 311 determines that user is near a hazardous location. Based on this determination, a colour is indicated.

In an embodiment, the alert module may be used to alert the user in case of an emergency or in case of detection of at least one hazardous condition.

Figure 4:
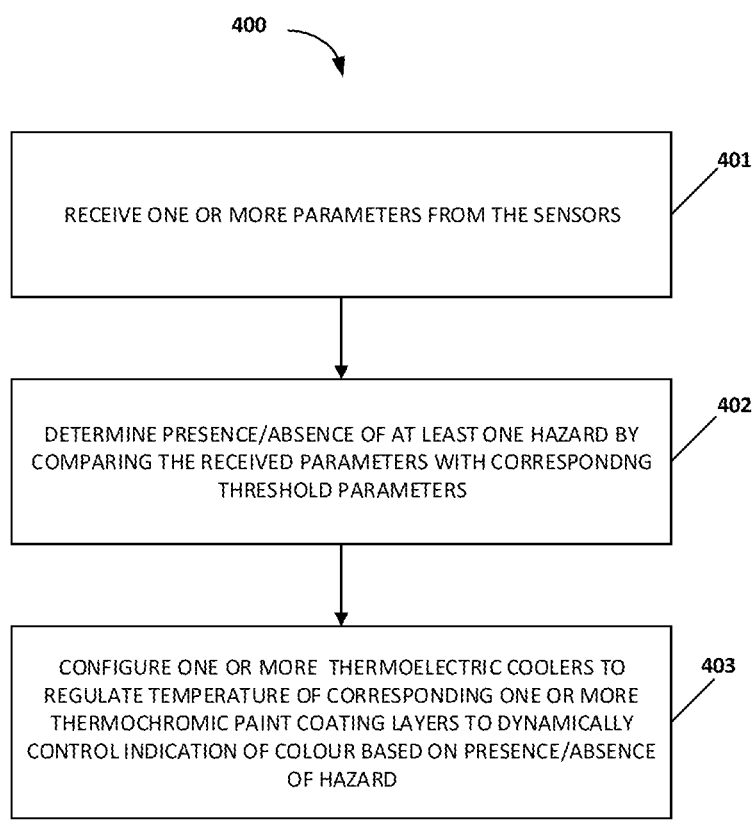
FIG. 4 shows an exemplary flow chart illustrating method steps for indicating hazardous condition with some embodiments of the present disclosure.

FIG. 4 shows a flow chart illustrating a method for indicating hazardous condition on the wearable device 100, in accordance with some embodiments of the present disclosure.

As illustrated in FIG. 4, the method 400 may comprise one or more steps for indicating hazardous condition on the wearable device 100, in accordance with some embodiments of the present disclosure. The method 400 may be described in the general context of computer executable instructions. Generally, computer executable instructions can include routines, programs, objects, components, data structures, procedures, modifies, and functions, which perform particular functions or implement particular abstract data types.

The order in which the method 400 is described is not intended to be construed as a limitation, and any number of the described method blocks can be combined in any order to implement the method. Additionally, individual blocks may be deleted from the methods without departing from the spirit and scope of the subject matter described herein. Furthermore, the method can be implemented in any suitable hardware, software, firmware, or combination thereof.

At step 401, receiving, by a control module 201 of the wearable device 100, one or more parameters, from one or more sensors 102 associated with the wearable device 100. The communication module 310 receives one or more parameters from the one or sensors 102 associated with the wearable device 100. The received one or more parameters may be stored as the sensor data 305.

At step 402, determining, by the control module, one of presence and absence of at least one hazardous condition by comparing the one or more parameters with corresponding threshold parameters. The determination module 311 determines one of presence and absence of the at least one hazardous condition. The one or more parameters obtained from the one or more sensors 102 are received by the communication module 310. The one of presence and absence of at least one hazardous condition is determined by comparing the one or more parameters obtained from step 402 with the corresponding one or more threshold values of one or more parameters, obtained from the threshold data 306. The comparison may show if the one or more parameters have varied from the corresponding one or more threshold values. The variation is used to determine one of presence and absence of at least one hazardous condition.

At step 403, configuring, by the control module, one or more thermoelectric couples to regulate temperature of corresponding one or more thermochromic paint coating layers, to dynamically control indication of colour, based on one of the presence and absence of the at least one hazardous condition. Upon determining the presence of the at least one hazardous condition, the control module 201 provides voltage to the corresponding one or more thermoelectric couples 203 such that the corresponding one or more thermoelectric couples 203 associated with the one or more thermochromic paint coating layers 202 dissipates heat. The heat generated from the corresponding one or more thermoelectric couples 203 increases the temperature of the corresponding one or more thermochromic paint coating layers 202, to indicate the particular colour. Each of the hazardous condition may be indicated by a particular colour. The indication of the particular colour, depends on activating the corresponding one or more thermoelectric couples 203 by providing it with appropriate voltage. Each of the one or more thermoelectric couples 203 may be associated with the corresponding one or more thermochromic paint coating layers 202 indicating a particular colour. When the at least one hazardous condition is determined, the control module 201 configures at least one thermoelectric couple 203 of the one or more thermoelectric couples 203 to activate the corresponding one or more thermochromic paint coating layers 202 designed to emit the colour assigned to the particular hazard.

In an embodiment, at step 403, on finding that the determined at least one hazardous condition has been resolved, the control module provides a reverse voltage to the corresponding one or more thermoelectric couples 203 such that the corresponding one or more thermoelectric couples 203 associated with the one or more thermochromic paint coating layers 202 cools down. The corresponding one or more thermoelectric couples 203 instantly decreases the temperature of the corresponding one or more thermochromic paint coating layers 202, to remove the particular colour displayed. Thus, implying that the determined at least one hazardous condition has been resolved.

In an embodiment, the method 400 may include, receiving a location from a localization module. The localization module provides the location information of the user. Based on the location of the user identified, the determination module 311 determines if the current location is hazardous depending on the distance between the current location of the user and the one or more predetermined hazardous locations. The activation module 312 configures the one or more thermoelectric couples 203 to regulate temperature of the corresponding one or more thermochromic paint coating layers 202, to dynamically control indication of the colour, based on the determination of the hazardous location.

In an embodiment, a visual monitoring system (not shown in Figure) such as floor cameras may capture the images of the wearable device and detect the colour changes of the one or more thermochromics coating layers 202. A processor of the exemplary system may determine whether an object of the image signal is a person, based on a size and an outline of the wearable device and detect the colour changes of the thermochromics coating layers. A central monitoring system (not shown in Figure) may take appropriate actions according to the colour changes.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise. The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated method of FIG. 4 show certain events occurring in a certain order. In alternative embodiments, certain operations may be performed in a different order, modified or removed. Moreover, steps may be added to the above described logic and still conform to the described embodiments. Further, operations described herein may occur sequentially or certain operations may be processed in parallel. Yet further, operations may be performed by a single processing unit or by distributed processing units.

In an embodiment, the disclosed system and method provides does not make use of radio frequencies (RF) for its operation compared to the existing solutions. Thus, the present device and method does not affect the workers wearing the wearable device 100 from harmful radiations.

In an embodiment, the system may be used to monitor a personnel in a hazardous environment with the help of a visual monitoring system (not shown in Figure) to identify the colour changes of the one or more thermochromic paint coating layer and generate appropriate alert messages.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERRAL NUMERALS

| Reference number | Description |
|---|---|
| 100 | Wearable device |
| 101 | Indication unit |
| 102 | One or more sensors |
| 201 | Control module |
| 202 | One or more thermochromic paint coating layers |
| 203 | One or more thermoelectric couples |
| 204 | Thermally conductive layer |
| 205 | Heat regulation layer |
| 206 | Thermally non-conductive layer |
| 301 | I/O interface |
| 302 | Memory |
| 303 | Processor |
| 304 | Data |
| 305 | Sensor data |
| 306 | Threshold data |
| 307 | Colour data |
| 308 | Other data |
| 309 | Modules |
| 310 | Communication module |
| 311 | Determination module |
| 312 | Activation module |
| 313 | Other modules |

What is claimed is:

1. A wearable device to indicate hazardous conditions, comprising:
one or more thermochromic paint coating layers, each indicative of a colour based on variations in temperature;
one or more thermoelectric couples to regulate the temperature of corresponding one or more thermochromic paint coating layers; and
a control module configured to:
receive one or more parameters from one or more sensors associated with the one or more thermoelectric couples;
determine one of presence and absence of at least one hazardous condition by comparing the one or more parameters with corresponding threshold parameters; and
configure the one or more thermoelectric couples to regulate temperature of the corresponding one or more thermochromic paint coating layers, to dynamically control indication of the colour, based on one of the presence and absence of the at least one hazardous condition.

2. The wearable device of claim 1, wherein the wearable device further comprises a thermal conductive layer between each of the one or more thermoelectric couples and the corresponding one or more thermochromic paint coating layers, for propagating heat from the one or more thermoelectric couples to the corresponding one or more thermochromic paint coating layers.

3. The wearable device of claim 1, wherein the one or more thermoelectric couples receives a voltage from the control module, to one of increase and decrease temperature of the corresponding one or more thermochromic paint coating layers.

4. The wearable device of claim 1, wherein the at least one hazardous condition is associated with a colour.

5. The wearable device of claim 1, wherein the one or more thermoelectric couples increases the temperature of the corresponding one or more thermochromic paint coating layers, for displaying a colour when the at least one hazardous condition is present.

6. The wearable device of claim 5, wherein the one or more thermoelectric couples decreases the temperature of the corresponding one or more thermochromic paint coating layers, for removing the displayed colour, when the at least one hazardous condition is resolved.

7. The wearable device of claim 1, wherein the wearable device further comprises a thermal regulation layer to one of dissipate heat and absorb heat, from the one or more thermoelectric couples.

8. The wearable device of claim 1, wherein the control module comprises a localization module configured to determine a location of a user, and wherein the one or more thermochromic paint coating layers indicates a colour corresponding to a distance between the location of the user and one or more predetermined hazardous locations.

9. The wearable device of claim 1, wherein the one or more parameters comprises at least one of environmental parameters and user parameters.

10. The wearable device of claim 1, wherein the one or more sensors comprises at least one of, a temperature sensor, a gas sensor, an accelerometer, a vibration sensor, a magnetometer, a core body temperature sensor, and a heart rate sensor.

11. A method for indicating hazardous conditions on a wearable device, comprising:
receiving, by a control module of a wearable device, one or more parameters, from one or more sensors associated with one or more thermoelectric couples of the wearable device;
determining, by the control module, one of presence and absence of at least one hazardous condition by comparing the one or more parameters with corresponding threshold parameters; and
configuring, by the control module, the one or more thermoelectric couples to regulate temperature of corresponding one or more thermochromic paint coating layers, to dynamically control indication of the colour, based on one of the presence and absence of the at least one hazardous condition.

12. The method of claim 11, wherein the at least one hazardous condition is associated with a colour.

13. The method of claim 11, wherein the one or more thermoelectric couples increases the temperature of the corresponding one or more thermochromic paint coating layers, for displaying a colour when the at least one hazardous condition is present.

14. The method of claim 13, wherein the one or more thermoelectric couples decreases the temperature of the corresponding one or more thermochromic paint coating layers, for removing the displayed colour, when the at least one hazardous condition is resolved.

15. The method of claim 11, further comprising determining, using a localization module, a location of a user, wherein the one or more thermochromic paint coating layers indicates a colour corresponding to a distance between the location of the user and one or more predetermined hazardous locations.

16. The method of claim 11, wherein the one or more parameters comprises one of environmental parameters and user parameters.

* * * * *